US009165178B2

(12) United States Patent
Higuchi

(10) Patent No.: US 9,165,178 B2
(45) Date of Patent: *Oct. 20, 2015

(54) DETERMINATION DEVICE, FINGERPRINT INPUT DEVICE, DETERMINATION METHOD AND DETERMINATION PROGRAM FOR DETECTING THE FORGERY OF A FINGER

(71) Applicant: NEC CORPORATION, Tokyo (JP)

(72) Inventor: Teruyuki Higuchi, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/280,893

(22) Filed: May 19, 2014

(65) Prior Publication Data
US 2014/0254895 A1 Sep. 11, 2014

Related U.S. Application Data

(62) Division of application No. 13/322,599, filed as application No. PCT/JP2010/059800 on Jun. 3, 2010, now Pat. No. 8,768,015.

(30) Foreign Application Priority Data

Jun. 8, 2009 (JP) ................... 2009-136817

(51) Int. Cl.
G06K 9/62 (2006.01)
G06K 9/00 (2006.01)
A61B 5/117 (2006.01)
G06T 1/00 (2006.01)

(52) U.S. Cl.
CPC ............ *G06K 9/0012* (2013.01); *A61B 5/1172* (2013.01); *G06K 9/00899* (2013.01); *G06T 1/0021* (2013.01)

(58) Field of Classification Search
None
See application file for complete search history.

(56) References Cited

U.S. PATENT DOCUMENTS 5,737,439 A 4/1998 Lapsley et al.
6,292,576 B1 9/2001 Brownlee
(Continued)

FOREIGN PATENT DOCUMENTS

CN 1493255 5/2004
EP 0372748 6/1990
(Continued)

OTHER PUBLICATIONS

International Search Report, PCT/JP2010/059800 dated Jul. 6, 2010.
(Continued)

*Primary Examiner* — Brian P Werner
(74) *Attorney, Agent, or Firm* — Young & Thompson

(57) ABSTRACT

A device is not able to detect the forgery of a finger with high accuracy by the comparison of a reflected light image and a transmitted light image that are obtained from the same finger. A determination device is provided with an input means for receiving the reflected light image obtained by photographing a fingerprint of a finger with light reflected from the surface of the finger and the transmitted light image obtained by photographing the fingerprint of the finger with light transmitted through the finger, and a determination means for comparing the reflected light image and the transmitted light image, and outputting a real-forgery determination result of the fingerprint of the finger.

14 Claims, 8 Drawing Sheets

(56) References Cited

U.S. PATENT DOCUMENTS

| | | |
|---|---|---|
| 6,927,844 B2 | 8/2005 | Higuchi et al. |
| 7,254,255 B2 | 8/2007 | Dennis |
| 7,627,151 B2 | 12/2009 | Rowe |
| 7,783,088 B2 | 8/2010 | Shinzaki et al. |
| 2007/0211926 A1 | 9/2007 | Shinzaki et al. |
| 2007/0223791 A1 | 9/2007 | Shinzaki |

FOREIGN PATENT DOCUMENTS

| | | |
|---|---|---|
| EP | 1353292 | 10/2003 |
| EP | 1894524 | 3/2008 |
| JP | 61283994 | 12/1986 |
| JP | 2007122237 | 5/2007 |
| JP | 2007179434 | 7/2007 |
| JP | 2007249296 | 9/2007 |
| JP | 2007259964 | 10/2007 |
| JP | 2008067727 | 3/2008 |
| JP | 2008305427 | 12/2008 |
| JP | 4501161 | 7/2010 |
| JP | 4599320 | 12/2010 |
| JP | 4757071 | 8/2011 |
| JP | 4760870 | 8/2011 |
| WO | 00/28469 | 5/2000 |

OTHER PUBLICATIONS

Extended European Search Report dated Nov. 20, 2012, Application No. 10786202.1.

Chinese Office Action dated Jun. 6, 2014, in corresponding Chinese Patent Application No. 201080025323.6.

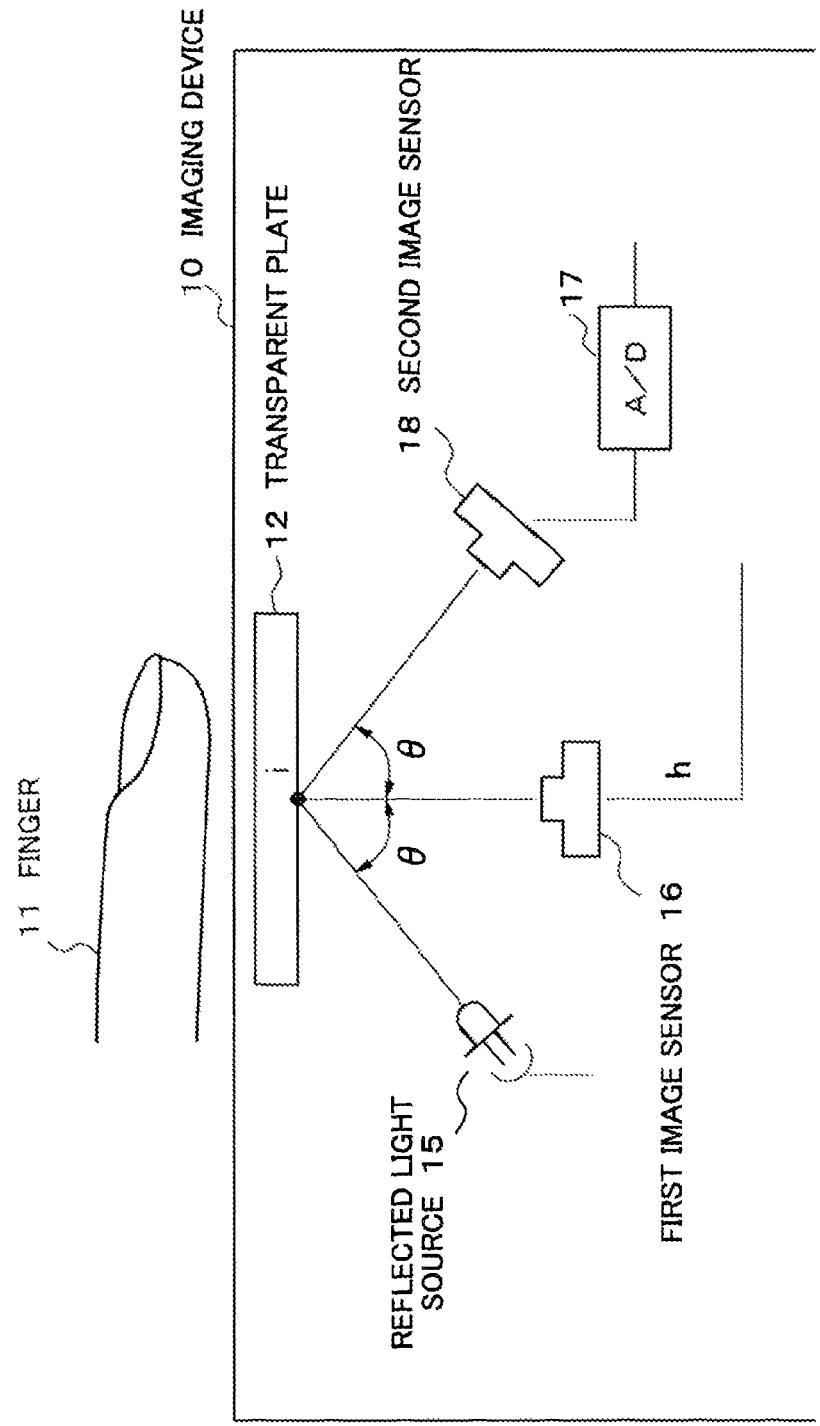

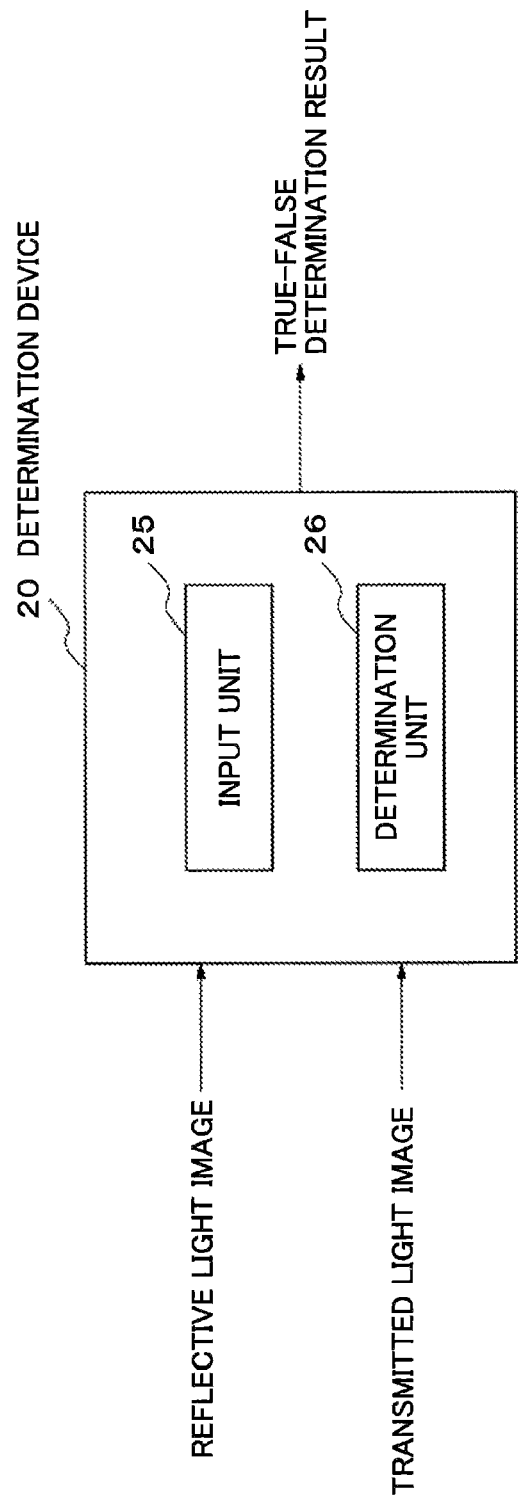

DETERMINATION DEVICE, FINGERPRINT INPUT DEVICE, DETERMINATION METHOD AND DETERMINATION PROGRAM FOR DETECTING THE FORGERY OF A FINGER

CROSS REFERENCE TO RELATED APPLICATIONS

This application is a division of application Ser. No. 13/322,599 filed on Nov. 28, 2011, which is a National Stage of PCT/JP2010/059800 filed on Jun. 3, 2010, which claims foreign priority to Japanese Application No. 2009-136817 filed on Jun. 8, 2009. The entire contents of each of the above applications are hereby incorporated by reference.

TECHNICAL FIELD

The present invention relates to a determination device, a fingerprint input device, a determination method and a determination program.

BACKGROUND ART

In patent document 1, there is described a device for determining a photographic subject to be a forged finger when the color of an image acquired by reflecting visible light of forgery determination illumination to the subject is not equal to the color of a finger image registered with a data recording means in advance. The device performs personal identification by collating minutia features acquired from transmitted light by applying near-infrared light of personal identification illumination to a finger with the minutia features of a finger image which is acquired in the same way and registered with a data recording means in advance.

In patent document 2, there is disclosed a device which, by switching white light and infrared light selectively, acquires a fingerprint image by reflecting the white light on a surface part of a finger, acquires a vein image by making the infrared light enter inside the finger and be scattered, and, by comparing each of them with a registered fingerprint image and a registered vein image, certifies a specific person.

In patent document 3, a device which determines a forged finger by comparing a fingerprint image taken with a high sensitivity and a fingerprint image taken with a low sensitivity is disclosed.

In patent document 4, a device which determines whether a finger vein image is of a living body or not based on a difference between finger vein pictures imaged by transmitted light having different wavelengths is disclosed.

CITATION LIST

Patent Document

[Patent document 1] Japanese Patent Application Laid-Open No. 2007-122237
[Patent document 2] Japanese Patent Application Laid-Open No. 2007-179434
[Patent document 3] Japanese Patent Application Laid-Open No. 2007-259964
[Patent document 4] Japanese Patent Application Laid-Open No. 2008-67727

DISCLOSURE OF THE INVENTION

Problems to be Solved by the Invention

The technologies in the above patent documents cannot detect forgery of a finger with high accuracy because they depend on comparison of a reflected light image and a transmitted light image obtained from an identical finger. The technology described in patent document 1 performs real-forgery determination by comparing a reflected light image of a photographic subject and that of a real finger. The technology described in patent document 2 only performs image comparison of a finger of a collation target and a real finger, and, in addition to that, it does not determine true or false of a fingerprint of a finger in first place. In patent document 3, there even is no citation of a reflected light image and a transmitted light image. The technology described in patent document 4 is one which performs comparison between transmitted light images of an identical finger.

An object of the present invention is to provide a determination device, a fingerprint input device, a determination method and a determination program which solve the above-mentioned problem.

Means for Solving the Problem

A determination device in an exemplary embodiment of the invention comprises an input means for receiving a reflected light image obtained by photographing a fingerprint of a finger by light reflected by a surface of the finger and a transmitted light image obtained by photographing the fingerprint of the finger by light transmitted through the finger; and a determination means for comparing the reflected light image and the transmitted light image and outputting a real-forgery determination result of the fingerprint of the finger.

A determination program in an exemplary embodiment of the invention causes a computer to carry out processing of receiving a reflected light image obtained by photographing a fingerprint of a finger by light reflected by a surface of the finger and a transmitted light image obtained by photographing the fingerprint of the finger by light transmitted through the finger, and outputting a real-forgery determination result of the fingerprint of the finger by comparing the reflected light image and the transmitted light image.

A determination method in an exemplary embodiment of the invention comprises, receiving a reflected light image obtained by photographing a fingerprint of a finger by light reflected by a surface of the finger and a transmitted light image obtained by photographing the fingerprint of the finger by light transmitted through the finger; comparing the reflected light image and the transmitted light image; and outputting a real-forgery determination result of the fingerprint of the finger.

Effect of the Invention

A determination device determines forgery of a finger with a high degree of accuracy using a characteristic difference between an image obtained by reflected light and an image obtained by transmitted light.

BRIEF DESCRIPTION OF THE DRAWINGS

FIG. 5 is a partial block diagram of an imaging device 10 according to the second exemplary embodiment.

FIG. 7 is a block diagram of a determination device 20 according to the fourth exemplary embodiment.

DESCRIPTION OF SYMBOLS

Figure 1:
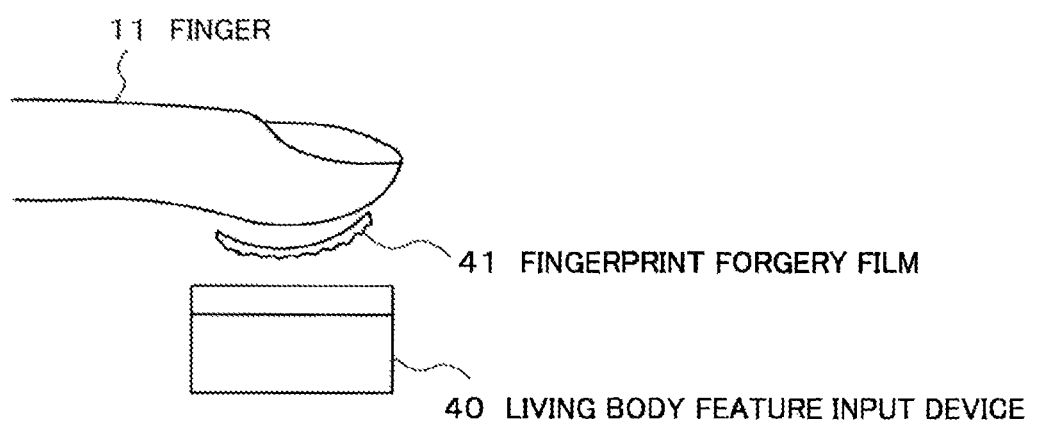
FIG. 1 is a diagram illustrating a fingerprint forgery film 41.

10 Imaging device
11 Finger
12 Transparent plate
13 First transmitted light source
14 Second transmitted light source
15 Reflected light source
16 First image sensor
17 A/D converter
18 Second image sensor
19 Infrared cut filter
20 Determination device
21 Computer
22 Processor
23 Memory
24 Driving means
25 Input unit
26 Determination unit
29 Determination program
30 Fingerprint input device
40 Living body feature input device
41 Fingerprint forgery film Most Preferred Exemplary Embodiment for Carrying out the Invention A living body feature input device 40 for certifying an individual using a fingerprint reads unevenness of a skin surface. Accordingly, it has been difficult for the living body feature input device 40 to find out an act such as to "disguise" as another person by sticking a semitransparent fingerprint forgery film 41 having unevenness as shown in FIG. 1 on the tip of a real finger 11. Such a malicious act can be also performed by a finger 11 that is counterfeited by resin, such as silicon, having unevenness. The fingerprint input device 30 of this exemplary embodiment prevents an act such as "disguise" mentioned above by performing real-forgery determination of the fingerprint of the finger 11.

Figure 2:
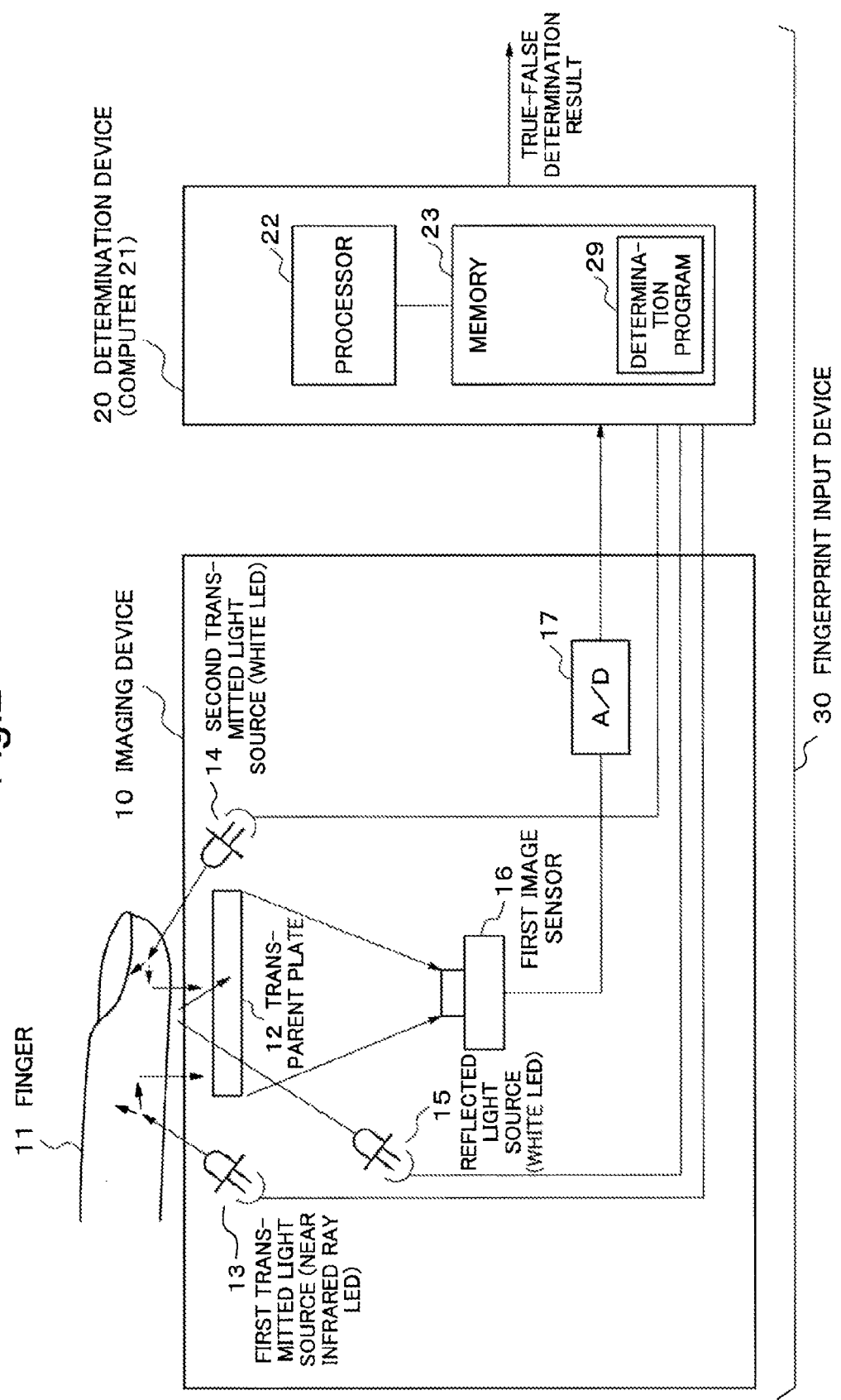
FIG. 2 is a block diagram of a fingerprint input device 30 according to the first exemplary embodiment.

FIG. 2 is a block diagram of the fingerprint input device 30 according to this exemplary embodiment. The fingerprint input device 30 includes: an imaging device 10 which acquires and outputs a fingerprint image of the finger 11; and a determination device 20 that performs real-forgery determination of the fingerprint of the finger 11 and outputs a determination result.

The imaging device 10 includes a transparent plate 12, the first transmitted light source 13, the second transmitted light source 14, a reflected light source 15, the first image sensor 16 and an A/D converter 17 (Analog/Digital). The finger 11 is placed on the upper part, touching the transparent plate 12.

The first transmitted light source 13 is an LED (Light Emitting Diode) which issues an infrared ray or a near infrared ray, for example. The second transmitted light source 14 is visible light such as a white LED which issues white light. The first transmitted light source 13 and the second transmitted light source 14 are placed around the transparent plate 12, and radiate the finger 11 from a side, a tip and the like.

Visible light such as a white LED which issues white light is preferably used as the reflected light source 15. On the presupposition of color analysis by a spectrum analysis or the like, the reflected light source 15 may be a light source of other kind of light than visible light. The reflected light source 15 is placed in a portion which is bellow the transparent plate 12 (on the other side of the transparent plate 12 from the contact surface of the finger 11) and is situated in an oblique direction from the transparent plate 12 (in a outwardly direction from the place where the finger 11 is placed on the transparent plate 12), and illuminates the finger 11 from below. The reflected light source 15 is placed in a position which allows reflected light of the finger 11 to enter the first image sensor 16.

An LED which issues an infrared ray or a near infrared ray is an LED of a wavelength band of 850-960 nm commonly used in an infrared ray remote controller and the like, for example. A white LED is one constituted of LEDs of three primary colors of red, blue and green, for example, or an LED using fluorescent emission of blue or ultraviolet color.

The first image sensor 16 is a color image sensor having sensitivities up to the near infrared ray area, for example. The A/D converter 17 digitalizes analog image data obtained by the first image sensor 16 and transmits it to the determination device 20.

When the first transmitted light source 13 lights up and is radiating a near infrared ray or the like to the real finger 11, the near infrared ray or the like is scattered inside the finger 11, and, by near-infrared light radiated from skin, the first image sensor 16 obtains a good fingerprint image. The reason of this is that a near infrared ray penetrates through the living body well.

When the second transmitted light source 14 lights up and is radiating white light or the like to the real finger 11, the white light or the like is scattered inside the finger 11, and, by white light or the like radiated from skin, the first image sensor 16 obtains a fingerprint image which is red reflecting the color of the blood.

Meanwhile, in order to obtain a fingerprint image by a near infrared ray or white light scattering and penetrating inside the real finger 11, it is desirable to press the finger 11 onto the transparent plate 12 so that blood in the pressed side of the finger 11 is moved to the side or the like of the finger 11 as much as possible. The reason is that it can prevent a blood vessel such as a vein from being imaged.

When the reflected light source 15 lights up and is radiating white light or the like to the real finger 11, the white light or the like is reflected at the surface of the finger 11, and, by white light or the like radiated from skin, the first image sensor 16 obtains a reflected light image with the color of the skin. In other words, the reflected light source 15 is placed in a position by which a reflected light image is obtained on the first image sensor 16.

The determination device 20 receives from the imaging device 10 three kinds of fingerprint images of the identical finger 11 obtained by the first image sensor 16 using the three kinds of light sources, performs real-forgery determination of the fingerprint of the finger 11 by analyzing the characteristics of each image and by comparing these, and outputs a determination result signal.

A real-forgery determination result which the determination device 20 outputs is inputted to the living body feature input device 40 that is not illustrated, for example. When the real-forgery determination result is "true" (the finger 11 is a real one), for example, the living body feature input device 40 performs authentication of an individual using the fingerprint of the finger 11. When the real-forgery determination result is "true", the determination device 20 may output all or part of the three kinds of fingerprint images received from the imaging device 10 to the living body feature input device 40. Also, when the real-forgery determination result is "true", the determination device 20 may perform personal authentication.

In order to input three kinds of above-mentioned fingerprint images, the determination device 20 controls turning on and off of the three kinds of light sources (the first transmitted light source 13, the second transmitted light source 14 and the reflected light source 15). However, it may be also configured such that turning on and off of the three kinds of light sources is controlled not by the determination device 20, but by the imaging device 10 autonomously, and the imaging device 10 acquires three kinds of fingerprint images and transmits these to the determination device 20 successively.

The determination device 20 may be realized by logic circuits as a dedicated device. For example, the determination device 20 may includes: an input unit 25 which receives fingerprint images from the imaging device 10; and a determination unit 26 which performs real-forgery determination of a fingerprint of the finger 11 by analyzing characteristics of each of the images and by comparing the images, and outputs a determination result signal. It may be also realized by a processor 22 of a computer 21 functioning as the determination device 20 by reading and executing a determination program 29 stored in a memory 23.

Figure 3:
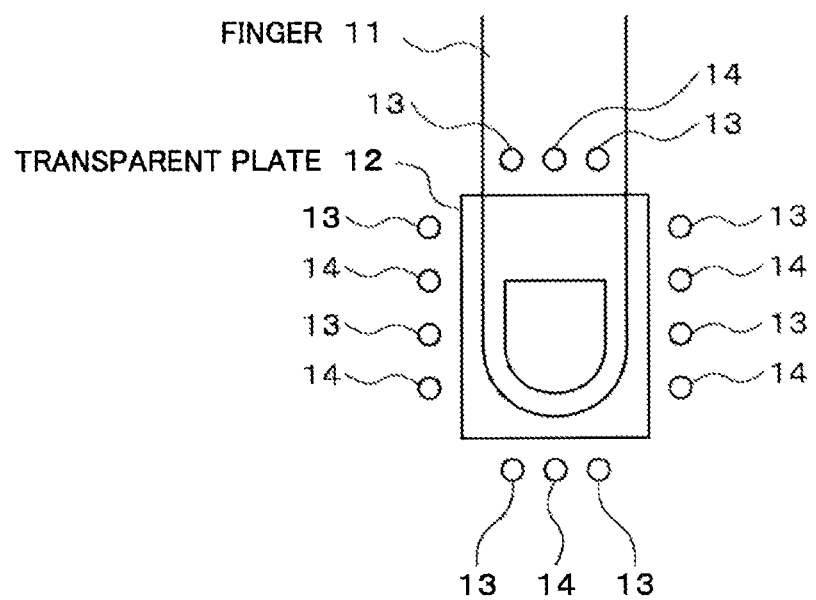
FIG. 3 is a diagram of an arrangement example of the first transmitted light source and the second transmitted light source.

FIG. 3 is a diagram of an arrangement example of the first transmitted light source 13 and the second transmitted light source 14. The first transmitted light source 13 and the second transmitted light source 14 are placed alternately along the periphery of the transparent plate 12, for example, and a near infrared ray and white light is applied to the finger 11 from the tip and the sides of the finger 11, from the lower side near the first joint of the finger 11 and the like.

Figure 4A:
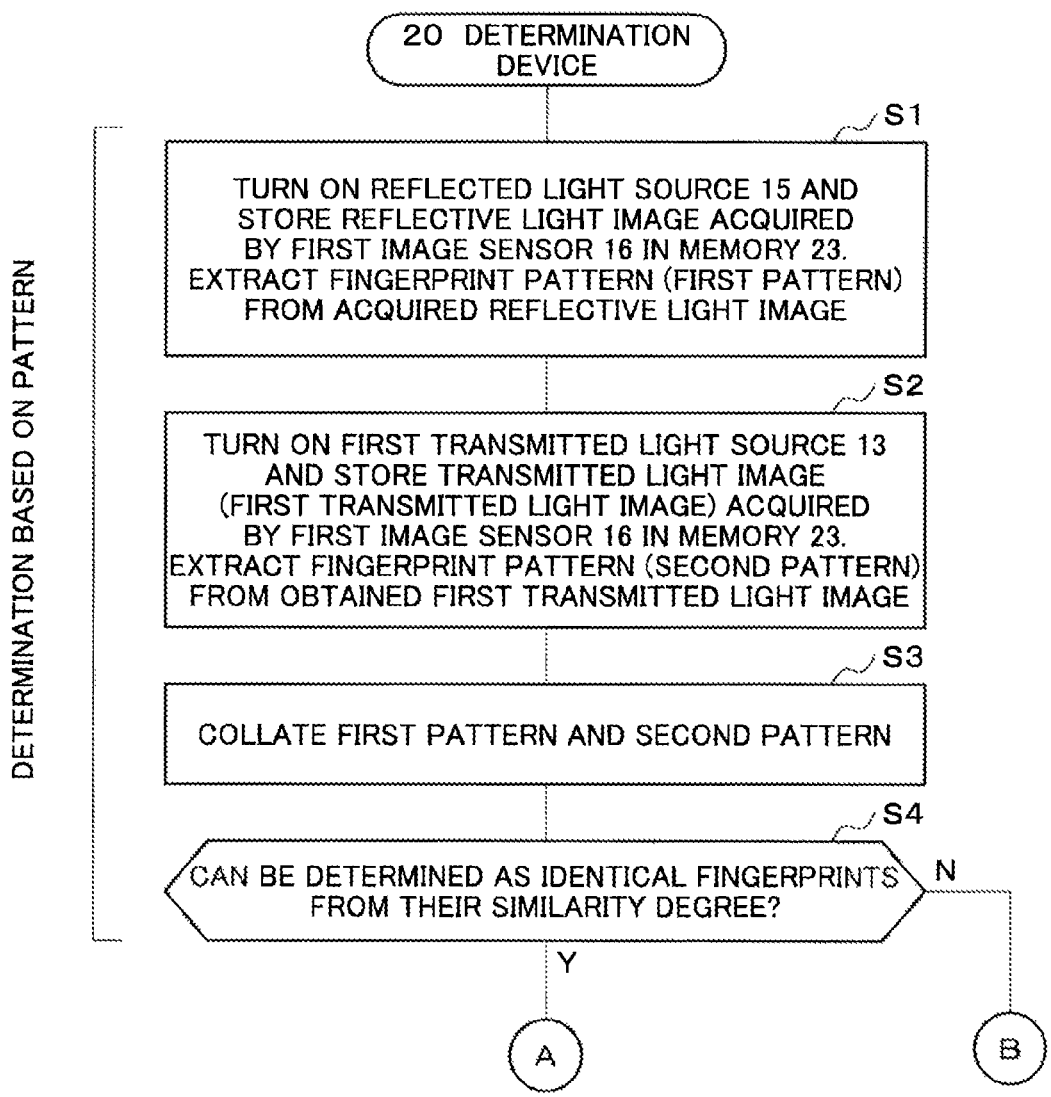
FIG. 4A is an operation flow chart (1/2) of a determination device 20.
Figure 4B:
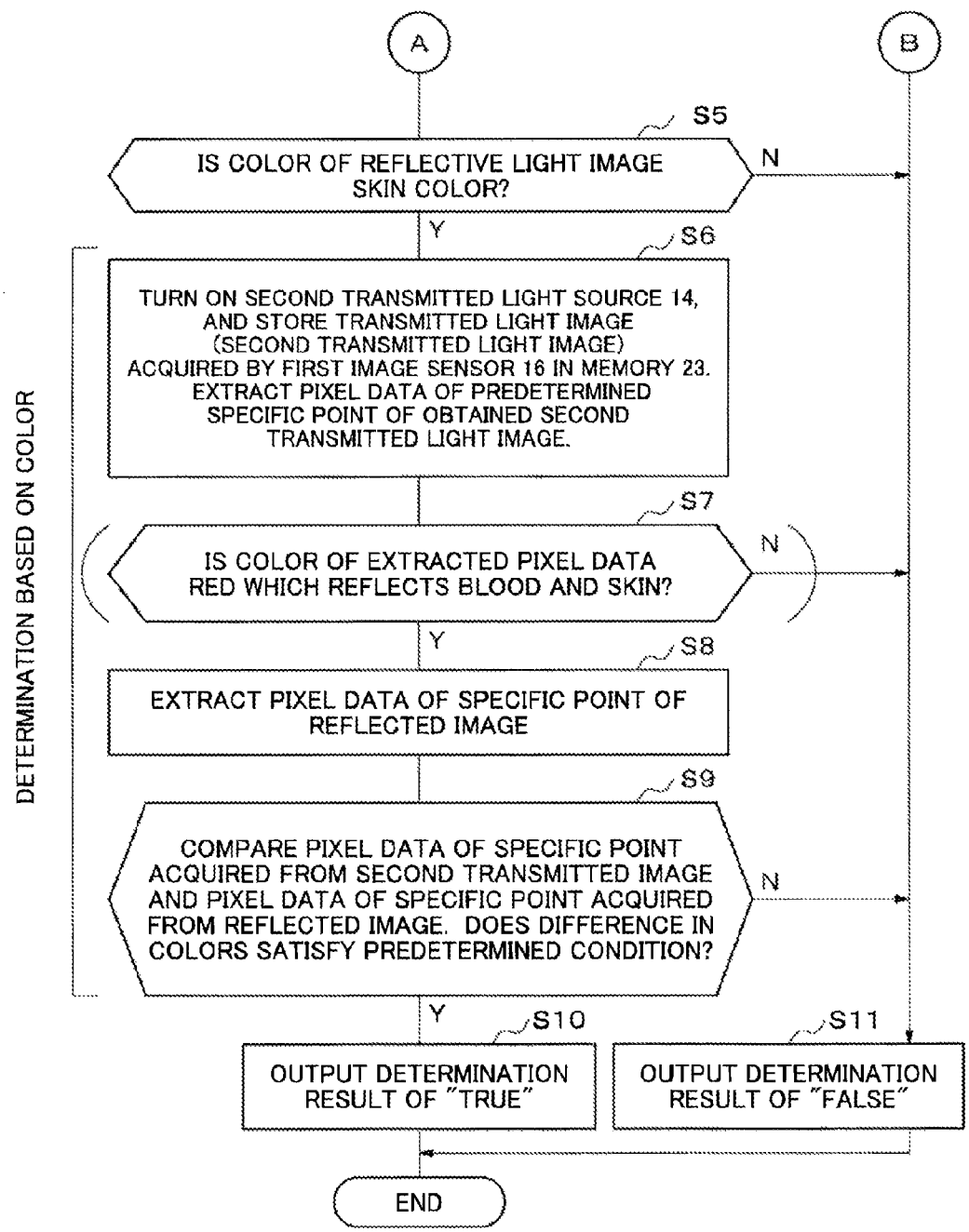
FIG. 4B is an operation flow chart (2/2) of the determination device 20.

FIG. 4A and FIG. 4B are operation flowcharts of the determination device 20. Here, it is supposed that all of the three kinds of light sources are turned off in the initial state as the premise.

The determination device 20 turns on the reflected light source 15 and stores a reflected light image acquired by the first image sensor 16 in the memory 23. Next, the determination device 20 extracts a fingerprint pattern (the first pattern) from the acquired reflected light image (S1). The determination device 20 turns the reflected light source 15 off after acquisition of the reflected light image.

The determination device 20 turns on the first transmitted light source 13 and stores a transmitted light image (the first transmitted light image) acquired by the first image sensor 16 in the memory 23. Next, the determination device 20 extracts a fingerprint pattern (the second pattern) from the obtained first transmitted light image (S2). The determination device 20 turns the first transmitted light source 13 off after acquisition of the first transmitted light image.

The determination device 20 collates the first pattern and the second pattern (S3). When determining from their similarity degree that they are identical fingerprints (Y in S4), the determination device 20 advances towards the next step. When it cannot determine that they are identical fingerprints (N in S4), the determination device 20 outputs a determination result which says "false" (S11), and finishes the operation. That is, the determination device 20 determines the finger 11 as a forgery.

When the semitransparent fingerprint forgery film 41 is stuck on the real finger 11, the determination device 20 extracts the fingerprint (unevenness) pattern of the counterfeit film 41 from a reflected light image. On the other hand, from the first transmitted light image, the determination device 20 detects a doubled pattern in which the fingerprint pattern of the real finger 11 and the fingerprint (unevenness) pattern of the counterfeit film 41 are overlapped. For this reason, the determination device 20 does not determine the both as identical fingerprints.

When the fingerprint forgery film 41 is opaque by a reason of being thick or the like, the determination device 20 does not determine the both as identical fingerprints, because a fingerprint pattern is not detected from the first transmitted light image. This applies to a case where the finger 11 is a forgery formed out of an opaque substance.

Meanwhile, the determination device 20 may output a determination result of "false" when, by comparing the number of minutia features extracted from a particular region of the first transmitted light image and the number of minutia features of the particular region extracted from the reflected light image, the former is larger than the latter by a predetermined value or a predetermined ratio. The predetermined value or the predetermined ratio is given to the determination device 20 as a system parameter or the like.

The determination device 20 can identify the particular region based on a box, a mark or a scale drawn on the transparent plate 12. The determination device 20 may identify the particular region based on a relative distance from the first joint or a fingerprint pattern (such as a circle of radius r from the center of a whorl).

In the case of Y in S4, the determination device 20 determines whether the color of the reflected light image is skin color or not, and when it is skin color (Y in S5), it advances to the next step. When it is not skin color (N in S5), the determination device 20 outputs a determination result which says "false" (S11), and finishes operating.

In the case of Y in S5, the determination device 20 turns on the second transmitted light source 14, and stores a transmitted light image (the second transmitted light image) acquired by the first image sensor 16 in the memory 23. Next, the determination device 20 extracts pixel data of a predetermined specific point of the obtained second transmitted light image (S6).

The determination device 20 can identify the specific point based on a box, a mark or s scale drawn on the transparent plate 12. The determination device 20 may identify the specific point based on a relative position from the center of the first joint or a fingerprint pattern (such as the center of a whorl). The number of specific points may be one or may be more than one. Further, a specific point may be selected from minutia features, or it may be selected from points other than minutia features.

The determination device 20 determines whether the color of the extracted pixel data is red which reflects blood and skin, and, when it is that color, advances toward the next step (Y in S7). When it is not such color (N in S7), the determination device 20 outputs a determination result which says "false" (S11), and finishes operating. Transmitted light obtained from the finger 11 counterfeited by resin such as silicon can be detected here because its color is not red which reflects blood and skin. A red color that reflects blood and skin is given to the determination device 20 as a system parameter based on actual measurement values about a large number of real fingers 11, for example.

In the case of Y in S7, the determination device 20 extracts pixel data of the specific point of the reflected image (S8). The determination device 20 compares pixel data of the specific point acquired from the second transmitted image and pixel data of the specific point acquired from the reflected image, and determines whether the difference in the colors satisfies a predetermined condition (S9). When the predetermined condition is satisfied (in S9, Y), the determination device 20 outputs a determination result that says "true" (S10), and finishes operating. When the predetermined condition is not satisfied (in S9, N), the determination device 20 outputs a determination result which says "false" (S11), and finishes operating.

The predetermined condition is a condition which describes a difference between the color of the specific point acquired from the second transmitted image (the color in which the color of skin and the color of blood is superposed) and the color of the specific point acquired from a reflected image (the color of the skin). For example, the condition is such that, in RGB color co-ordinates, a difference between the above colors should be no more than a fixed value c1 about green and blue, and, on the other hand, about red, a difference between the both should be a fixed value c2 ($>$c1) or more. Here, as for the fixed values c1 and c2, numerical values determined based on measurement are given to the determination device 20 as system parameters, for example.

The fingerprint input device 30 of this exemplary embodiment can perform real-forgery determination of a fingerprint of the finger 11 with a high degree of accuracy. The fingerprint input device 30 of this exemplary embodiment does not need to register a fingerprint image of the real finger 11 in advance in order to perform real-forgery determination of the fingerprint of the finger 11. That is, the fingerprint input device 30 of this exemplary embodiment can also perform real-forgery determination about the finger 11 inputted for the first time.

The reason is that three kinds of fingerprint images are acquired from the identical finger 11 using three kinds of light sources, and real-forgery determination is performed based on the characteristics of each of them or on comparison results between or among more than one of them.

The determination device 20 may carry out only either one of determination of steps S1 to S4 (determination based on pattern), or determination of steps S6 to S9 (S7 can be omitted) (determination based on color) to perform real-forgery determination of a fingerprint of the finger 11.

When only the determination based on pattern is carried out, the second transmitted light source 14 is unnecessary and the first image sensor 16 does not have to be a color image sensor. When only the determination based on color is carried out, the first transmitted light source 13 is unnecessary.

Further, it may be such that the fingerprint input device 30 does not include the imaging device 10, and a fingerprint image which has been already imaged and stored is acquired from a storage medium or a server or the like connected via a network.

FIG. 5 is a partial block diagram of an imaging device 10 according to the second exemplary embodiment. The imaging device 10 of this exemplary embodiment has a structure in which the second image sensor 18 and its A/D converter 17 are added to the imaging device 10 according to the first exemplary embodiment.

The second image sensor 18 is placed in a position symmetric to the reflected light source 15 about a line h which takes the first image sensor 16 as a starting point and is orthogonal to the transparent plate 12 at a point i. That is, a line to the reflected light source 15 and a line to the second image sensor 18, the both having the point i as a starting point, are at about an angle θ to the line h.

The imaging device 10 of this exemplary embodiment receives light that is emitted from the reflected light source 15 and is totally reflected by the transparent plate 12 by the second image sensor 18, and outputs a reflected light image. The other points are not different from the first exemplary embodiment.

By the reflected light source 15, the imaging device 10 of this exemplary embodiment can obtain a fingerprint image of a high contrast. The fingerprint input device 30 equipped with the imaging device 10 of this exemplary embodiment can be used even for real-forgery determination of a fingerprint of the finger 11 of a race and the like with the finger 11 in which melanin pigment ranges. The reason of this is that the second image sensor 18 receives a total reflection beam in which light in the contact zone is scattered by the fingerprint pattern of the finger 11 touching the transparent plate 12 at the contact zone, and output a reflected image.

Figure 6:
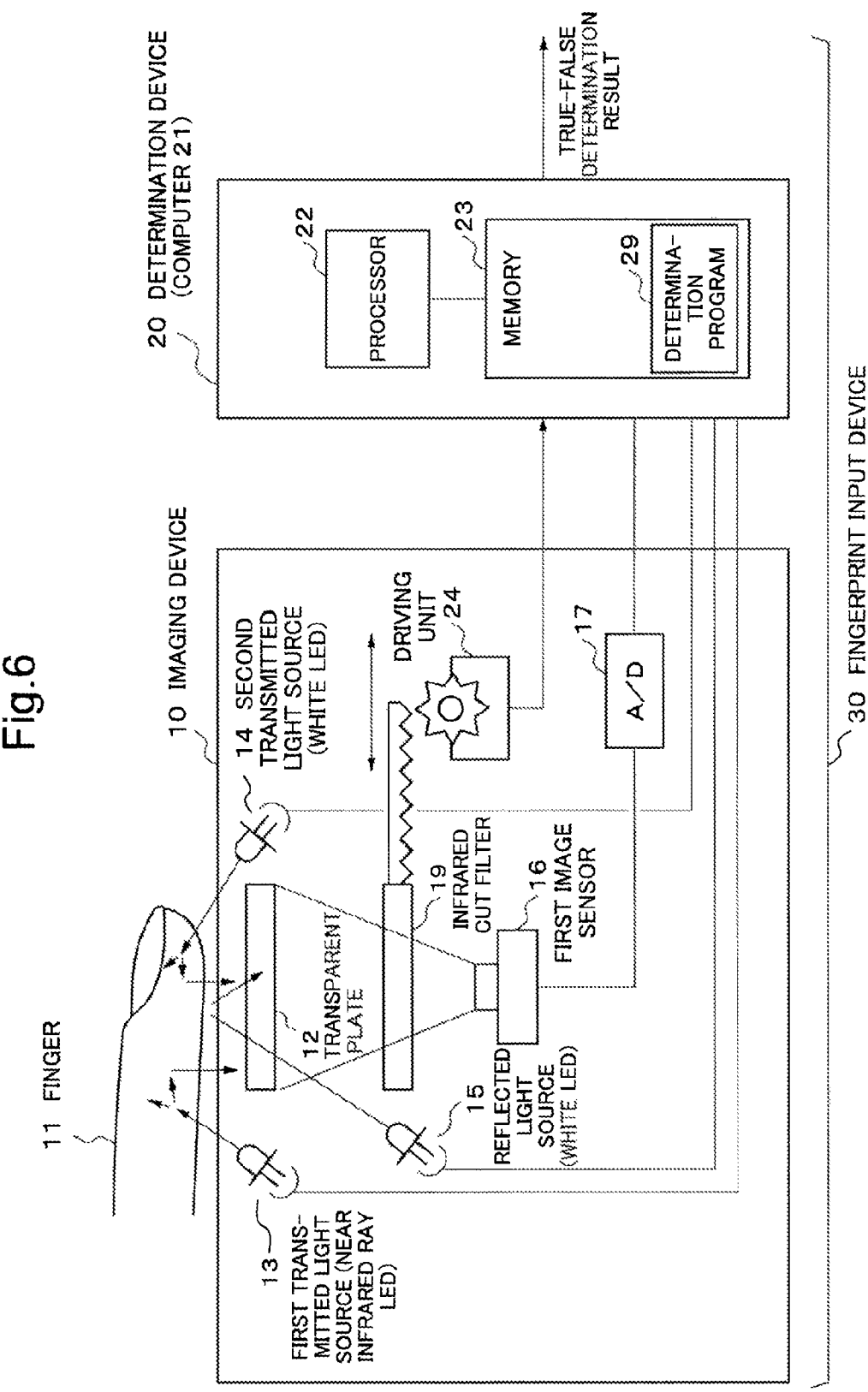
FIG. 6 is a block diagram of a fingerprint input device 30 according to the third exemplary embodiment.

FIG. 6 is a block diagram of the fingerprint input device 30 according to the third exemplary embodiment. The imaging device 10 of this exemplary embodiment is such that a movable infrared cut filter 19 and its driving unit 24 are added to the imaging device 10 according to the first exemplary embodiment.

Under directions of the determination device 20, for example, the driving means 24 moves the infrared cut filter 19 between: a position where the infrared cut filter 19 interrupts an optical path between the transparent plate 12 and the first image sensor 16 (the first position); and a position where it does not interrupt the optical path (the second position).

When the reflected light source 15 is lit (when outputting a reflected image) and when the second transmitted light source 14 is lit (when outputting the second transmitted image), the imaging device 10 of this exemplary embodiment moves the infrared cut filter 19 to the first position, and interrupts the optical path. On the other hand, when the first transmitted light source 13 is lit (when outputting the first transmitted image), the imaging device 10 moves the infrared cut filter 19 to the second position, and does not interrupt the optical path.

At the time of fingerprint image acquisition by a near infrared ray, without using the infrared cut filter 19, the fingerprint input device 30 of this exemplary embodiment can obtain a clear fingerprint image using a near infrared ray area. On the other hand, at the time of fingerprint image acquisition by white light, the fingerprint input device 30 can acquire a clear color picture using the infrared cut filter 19.

FIG. 7 is the fourth block diagram of the determination device 20 according to the present invention. The determination device 20 includes: the input unit 25 which inputs a reflected light image obtained by photographing a fingerprint of the finger 11 by light reflected by a surface of the finger 11 and a transmitted light image obtained by photographing the fingerprint of the finger 11 by light transmitted through the finger 11; and the determination unit 26 that compares the reflected light image and the transmitted light image and outputs a real-forgery determination result of the fingerprint of the finger 11.

The present invention is not limited to the above-mentioned exemplary embodiments. Various modifications which a person skilled in the art can understand can be made to the composition and details of the present invention within the scope of the present invention.

This application claims priority based on Japanese application Japanese Patent Application No. 2009-136817 filed on Jun. 8, 2009, the disclosure of which is incorporated herein in its entirety.

The invention claimed is:

1. A determination device comprising:
   an input circuit, which receives:
   a reflected light image obtained by photographing a fingerprint of a finger by light reflected by a surface of the finger, and a transmitted light image obtained by photographing the fingerprint of the finger by light transmitted through the finger; and a determination circuit, which compares a minutia extracted from the reflected light image and a minutia extracted from the transmitted light image and outputs a real-forgery determination result of the fingerprint of the finger.

2. The determination device according to claim 1, wherein the determination unit extracts a first fingerprint pattern from the reflected light image and extracts a second fingerprint pattern from a first transmitted light image photographed using infrared light, and when the first fingerprint pattern and the second fingerprint pattern are similar, determines the fingerprint of the finger as a real one, and when the first fingerprint pattern and the second fingerprint pattern are not similar, determines the fingerprint of the finger as a forgery.

3. The determination device according to claim 1, wherein the determination unit extracts a minutia from each of the reflected light image and a second transmitted light image photographed using visible light, and determines the fingerprint of the finger as a real one when a difference in colors of the minutiae satisfies a predetermined condition, and determines the fingerprint of the finger as a forgery when the difference does not satisfy the predetermined condition.

4. A fingerprint input device comprising:
the determination device according to claim 3 and;
an imaging device which
includes an optically transparent plate for placing the finger in a manner touching the plate, a first transmitted light source, placed around the plate, for radiating infrared light to the finger, a first image sensor, placed on an other side of the plate from the finger, apart from and facing the plate, a reflected light source, placed on the other side of the plate, apart from the plate in an outwardly oblique direction from a place where the finger is placed on the plate, for emitting visible light,
turns on one of the first transmitted light source and the reflected light source alternately and
outputs the first transmitted light image and the reflected light image formed on the first image sensor.

5. A fingerprint input device comprising:
the determination device according to claim 3 and;
an imaging device which includes an optically transparent plate for placing the finger in a manner touching the plate, a first transmitted light source, placed around the plate, for radiating infrared light to the finger, a first image sensor, placed on an other side of the plate from the finger, apart from and facing the plate, a reflected light source, placed on the other side of the plate, apart from the plate in an outwardly oblique direction from a place where the finger is placed on the plate, for emitting visible light, a second image sensor placed on the other side of the plate, apart from the plate, in a position symmetric to the reflected light source about a line passing the first image sensor and orthogonal to the plate,
turns on one of the first transmitted light source and the reflected light source alternately and
outputs the first transmitted light image formed on the first image sensor and the reflected light image formed on the second image sensor.

6. The fingerprint input device according to claim 5, wherein the first image sensor is a color image sensor and
the imaging device further includes a second transmitted light source, placed around the plate, for radiating visible light to the finger and turns on one of the first transmitted light source, the second transmitted light source and the reflected light source alternately, and outputs the first transmitted light image, the second transmitted light image and the reflected light image formed on the first image sensor.

7. A fingerprint input device comprising:
an image device which:
includes an optically transparent plate for placing the finger in a manner touching the plate, a second transmitted light source, placed around the plate, for radiating visible light to the finger, a first image sensor, placed on an other side of the plate from the finger, apart from and facing the plate, a reflected light source, placed on the other side of the plate, apart from the plate in an outwardly oblique direction from a place where the finger is placed on the plate, for emitting visible light;
turns on one of the second transmitted light source and the reflected light source alternately and
outputs a second transmitted light image and the reflected light image formed on the first image sensor; and
the determination device according to claim 1 which extracts a minutia from each of the reflected light image and the second transmitted light image, and, when a difference in colors of the minutiae satisfies a predetermined condition, determines the fingerprint of the finger as a real one, and when the difference does not satisfy the predetermined condition, determines the fingerprint of the finger as a forgery.

8. A determination device comprising:
a means for receiving a reflected light image obtained by photographing a fingerprint of a finger by light reflected by a surface of the finger and a transmitted light image obtained by photographing the fingerprint of the finger by light transmitted through the finger; and
a means for comparing a minutia extracted from the reflected light image and a minutia extracted from the transmitted light image and outputting a real-forgery determination result of the fingerprint of the finger.

9. A non-transient machine-readable medium which records a determination program causing a computer to carry out processing of receiving a reflected light image obtained by photographing a fingerprint of a finger by light reflected by a surface of the finger and a transmitted light image obtained by photographing the fingerprint of the finger by light transmitted through the finger, and outputting a real-forgery determination result of the fingerprint of the finger by comparing a minutia extracted from the reflected light image and a minutia extracted from the transmitted light image.

10. The non-transient machine-readable medium according to claim 9 which records the determination program causing the computer to carry out processing of extracting a first fingerprint pattern from the reflected light image and a second fingerprint pattern from a first transmitted light image photographed using infrared light, and determining the fingerprint of the finger as a real one when the both are similar, and determining the fingerprint of the finger as a forgery when the both are not similar.

11. The non-transient machine-readable medium according to claim 9 which records the determination program causing the computer to carry out processing of extracting a minutia from each of the reflected light image and a second transmitted light image photographed using visible light, and determining the fingerprint of the finger as a real one when a difference in colors of the minutiae satisfies a predetermined condition, and determining the fingerprint of the finger as a forgery when the difference does not satisfy the predetermined condition.

12. A determination method comprising: receiving a reflected light image obtained by photographing a fingerprint of a finger by light reflected by a surface of the finger and a transmitted light image obtained by photographing the fingerprint of the finger by light transmitted through the finger; comparing a minutia extracted from the reflected light image and a minutia extracted from the transmitted light image; and outputting a real-forgery determination result of the fingerprint of the finger.

13. The determination method according to claim 12, comprising the steps of: extracting a first fingerprint pattern from the reflected light image and a second fingerprint pattern from a first transmitted light image photographed using infrared light; and determining the fingerprint of the finger as a real one when the both are similar, and determining the fingerprint of the finger as a forgery when the both are not similar.

14. The determination method according to claim 12, comprising; extracting a minutia from each of the reflected light image and a second transmitted light image photographed using visible light; and determining the fingerprint of the finger as a real one when a difference in colors of the minutiae satisfies a predetermined condition, and determining the fingerprint of the finger as a forgery when the difference does not satisfy the predetermined condition.

* * * * *